US011674968B2

(12) United States Patent
E et al.

(10) Patent No.: US 11,674,968 B2
(45) Date of Patent: Jun. 13, 2023

(54) METHODS FOR IDENTIFYING FREE THIOLS IN PROTEINS

(71) Applicant: Regeneron Pharmaceuticals, Inc., Tarrytown, NY (US)

(72) Inventors: Sook Yen E, Croton-on-Hudson, NY (US); David Bramhall, New Milford, CT (US); Haibo Qiu, Hartsdale, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 528 days.

(21) Appl. No.: 16/745,020

(22) Filed: Jan. 16, 2020

(65) Prior Publication Data

US 2020/0225245 A1  Jul. 16, 2020

Related U.S. Application Data

(60) Provisional application No. 62/792,994, filed on Jan. 16, 2019.

(51) Int. Cl.
| | | |
|---|---|---|
| *G01N 33/68* | (2006.01) | |
| *A61K 39/395* | (2006.01) | |
| *G01N 1/28* | (2006.01) | |
| *G01N 30/72* | (2006.01) | |
| *G01N 30/02* | (2006.01) | |
| *G01N 30/88* | (2006.01) | |

(52) U.S. Cl.
CPC ....... *G01N 33/6848* (2013.01); *A61K 39/395* (2013.01); *G01N 1/28* (2013.01); *G01N 30/7233* (2013.01); *G01N 33/6854* (2013.01); *G01N 2030/027* (2013.01); *G01N 2030/8831* (2013.01); *G01N 2458/15* (2013.01)

(58) Field of Classification Search
CPC ........... G01N 33/6848; G01N 33/6854; G01N 33/6815; G01N 1/28; G01N 30/7233; G01N 2030/027; G01N 2030/8831; G01N 2458/15; A61K 39/395; A61K 2039/505
See application file for complete search history.

(56) References Cited

U.S. PATENT DOCUMENTS

| 9,835,629 | B2 | 12/2017 | Roger et al. |
| 2018/0106815 | A1 | 4/2018 | Barnridge et al. |

OTHER PUBLICATIONS

Mingyan Cao et al. (2018) "Characterization and analysis of scFv-IgG bispecific antibody size variants." mAbs (2018) 10:8 p. 1236-1247. (Year: 2018).*
Ambrogelly A et al. "Analytical comparability study of recombinant monoclonal antibody therapeutics." MAbs (2018) 10(4) 513-538. (Year: 2018).*
Araki, K., et al., "Redox Sensitivities of Global Cellular Cysteine Residues under Reductive and Oxidative Stress", J Proteome Res, 15(8): 2548-2559 (2016).
Clark, D.F., et al., "Simple Approach to Assign Disulfide Connectivity Using Extracted Ion Chromatograms of Electron Transfer Dissociation Spectra", Anal Chem, 85(2):1192-1199 (2013).
Furuki, et al., "Determination of thiol-to-protein ratio and drug-to-antibody ration by in-line size exclusion chromatography with post-column reaction", Anal Biochem, 527:33-44 (2017).
Giron, et al., "Cysteine tagging for MS-based proteomics", Mass Spectrometry Reviews, 30(3): 366-395 (2011).
Guo, Y., et al., "Counting sulfhydryls and disulfide bonds in peptides and proteins using mercurial ions as an MS-tag", Journal of the American Society for Mass Spectrometry, 19L1108-1113 (2008).
Lakbub, J., et al., "Disulfide bond characterization of endogenous IgG3 monoclonal antibodies using LC-MS: an investigation of IgG3 disulfide-mediated isoforms", Anal Meth, 8(31):6046-6055 (2016).
Lakbub, J., et al., "Recent mass spectrometry-based techniques and considerations for disulfide bond characterization in proteins", Coresta PTM Technical Report, Springer Beriin Heidelberg, DE, 410(10):2467-2484 (2017).
Li, et al., "Liquid chromatography and mass spectrometry with post-column partial reduction for the analysis of native and scrambled disulfide bonds", Anal Biochem, 439(2):184-186 (2013).
Liu, H., et al., "Characterization of Free Thiol Variants of an IgG1 by Reversed Phase Ultra High Pressure Liquid Chromatography Coupled With Mass Spectrometry", J Pharm Biomed Anal, 109:142-149 (2015).
Pan, Kuan-Ting, et al., "Mass Spectrometry-Based Quantitative Proteomics for Dissecting Multiplexed Redox Cysteine Modifications in Nitric Oxide-Protected Cardiomyocyte Under Hypoxia", Antiox Redox Signal, 20(9): 1365-1381 (2014).
Resemann, A., et al., "Rapid, automated characterization of disulfide bond scrambling and IgG2 isoform determination", mAbs, 10(8):1200-1213 (2018).
Seiwart, et al., "Differential labeling of free and disulfide-bound thiol functions in proteins", Journal of the American Society for Mass Spectrometry, 19:1-7 (2008).
Shakir, S., et al., "Quantitative analysis of the cysteine redoxome by iodoacetyl tandem mass tags", Anal Bioanal Chem, 409(15):3821-3830 (2017).
Wang, Y., et al., "Characterization and Comparison of Disulfide Linkages and Scrambling Patterns in Therapeutic Monoclonal Antibodies: Using LC-MS with Electron Transfer Dissociation", Anal Chem, 83(8):3133-3140 (2011).

(Continued)

*Primary Examiner* — Christopher Adam Hixson
(74) *Attorney, Agent, or Firm* — McCarter & English, LLP (57) ABSTRACT

Compositions and methods for identifying free thiols in protein are provided. An exemplary method labeling peptides with a tag to identify free thiols and a tag to identify native disulfide bonds and analyzing the tags using targeted MS². In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

22 Claims, 6 Drawing Sheets

(56) References Cited

OTHER PUBLICATIONS

The International Search Report and Written Opinion of the International Searching Authority, dated Apr. 28, 2020; 11 pages.
Eliuk, S., et al., "Evolution of Orbitrap Mass Spectrometry Instrumentation", Annu Rev Anal Chem., 8:61-80 (2015).
Feng, Y., et al., "Global analysis of protein structural changes in complex proteomes," Nat Biotechnol, 32(10):1036-1044 (2014).
Mortiz, et al., "Assessment of disulfide and hinge modifications in monoclonal antibodies", Electrophoresis, 36, 769-785 (2017).
Prudent, et al., "THe role of copper in cysteine oxidation: study of intra- and inter-molecular reactions in mass spectrometry", Metallomics, 1, 157-165 (2009).
Xiang, et al., "Localization and Quantitation of Free Sulfhydryl in Recombinant Monoclonal Antibodies by Differential Labeling with 12C and 13C Iodoacetic Acid and LC-MS Analysis," Anal Chern, 81, 8101-8108 (2009).
Yan, B., et al., "Human IgG1 Hinge Fragmentation as the Result of H2O2-mediated Radical Cleavage", J. Biol. Chem., 284:35390-35402 (2009).
Zheng, K., et al., "The impact of glycosylation on monoclonal antibody conformation and stability" mAbs 3:6, 568-576; (2011).

\* cited by examiner

Fig. 1A  iodoTMTsixplex reagents (4 of them are shown)

Fig. 1B  Schematic of Free Thiol Identification and Quantitation Workflow

METHODS FOR IDENTIFYING FREE THIOLS IN PROTEINS

CROSS-REFERENCE TO RELATED APPLICATIONS

This application claims benefit of and priority to U.S. Provisional Patent Application No. 62/792,994 filed Jan. 16, 2019, incorporated herein by reference in its entirety.

TECHNICAL FIELD OF THE INVENTION

The invention is generally related to systems and methods of characterizing free thiol group in proteins, particularly in antibodies.

BACKGROUND OF THE INVENTION

During the development of monoclonal antibodies (mAbs) from drug candidate to marketed product, issues with stability, post-translational modifications, or other changes to the antibody can occur. Alterations in antibody structure and function can cause problems such as poor shelf-life or even immunogenicity in the patient. It is therefore important to properly characterize antibody structure and monitor it throughout production. Antibody quality control and quality assurance are critical to the purity and safety of mAb products.

Disulfide bonds are important for structural integrity, stability, and biological functions of mAbs. Non-native disulfide bonds can cause changes in the structure and stability of mAbs. Binding affinity of mAbs to antigens can be affected by up to 50% if disulfide bonds are incomplete (Xiang, T., et al., *Anal Chem*, 81:8101-8108 (2009)). The low dissociation energy of disulfide bonds and the high flexibility of the hinge region frequently lead to modifications and cleavages at the hinge region (Moritz, B., and Stracke, J. O., *Electrophoresis*, 36:769-785 (2017)). In addition, administration of non-native disulfide bonded structures to humans has the potential to trigger unwanted immune responses. Analysis of disulfide bonds is therefore important for quality control assessment of mAbs. Current methods of analyzing mAb disulfide bonds are time-consuming and labor intensive.

Therefore, it is an object of the invention to provide systems and methods for characterizing antibodies, in particular disulfide bonds in monoclonal antibodies.

Another embodiment provides a method for identifying disulfide heterogeneity in a protein drug product.

It is another object of the invention to provide methods and compositions for identifying free thiols in proteins including but not limited to antibodies.

SUMMARY OF THE INVENTION

Compositions and methods for identifying free thiols (also referred to as free sulfhydryls) are provided. Free thiols can exist in proteins, for example mAbs, as a result of incomplete disulfide bond formation or disulfide bond breakage. The presence of free thiols can lower the thermal stability of mAb products and affect their structural integrity, stability, and biological functions. It is therefore important to characterize free thiols in mAb production. Methods for identifying site specific free thiols in protein drug products are disclosed herein. An exemplary method includes labeling peptides with a tag to identify free thiols and a tag to identify native disulfide bonds and analyzing the tags using targeted $MS^2$. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

One embodiment provides a method for identifying the presence of free thiols in a protein, for example an antibody or fragment thereof. An exemplary method for identifying free thiols in a protein drug product includes the steps of labeling a sample containing the protein drug product with a first label containing a sulfhydryl-reactive iodoacetyl group, an MS-neutral spacer arm, and a first MS/MS reporter having a unique reporter ion mass. Excess label can be removed and the sample is denatured and reduced. The sample is then labeled with a second label having a sulfhydryl-reactive iodoacetyl group, an MS-neutral spacer arm, and a second MS/MS reporter having a unique reporter ion mass. The method includes enzymatically digesting the sample and analyzing the sample using mass spectrometry, for example ultra-performance liquid chromatography tandem mass spectrometry system (UPLC-$MS^2$ system) including a charged surface hybrid column and a formic acid buffer mobile phase. Next, the method includes quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product. In one embodiment the first MS/MS reporter has a mass of 128 and the second MS/MS reporter has a mass of 131. The protein drug product is typically an antibody, for example a monoclonal or chimeric antibody. The presence of free thiols is likely a result of incomplete disulfide bond formation or disulfide bond degradation. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

Another embodiment provides a method of identifying disulfide heterogeneity in a protein drug product including the steps of labeling a sample containing the protein drug product with a first label containing a sulfhydryl-reactive iodoacetyl group, an MS-neutral spacer arm, and a first MS/MS reporter having a unique reporter ion mass. Excess label can be removed and the sample is denatured and reduced. The sample is then labeled with a second label having a sulfhydryl-reactive iodoacetyl group, an MS-neutral spacer arm, and a second MS/MS reporter having a unique reporter ion mass. The method includes enzymatically digesting the sample and analyzing the sample using mass spectrometry, for example an ultra-performance liquid chromatography tandem mass spectrometry system (UPLC-$MS^2$ system) including a charged surface hybrid column and a formic acid buffer mobile phase. Next, the method includes quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product. If the assay detects free thiols in the protein drug product, the protein drug product contains disulfide heterogeneity. The presence of these free thiols is likely a result of incomplete disulfide bond formation or disulfide bond degradation. In one embodiment the first MS/MS reporter has a mass of 128 and the second MS/MS reporter has a mass of 131. The protein drug product is typically an antibody, for example a monoclonal, chimeric antibody, bispecific antibody, or antigen binding fragments thereof. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

A method for selecting a protein drug product including the steps of labeling a sample containing the protein drug product with a first label containing a sulfhydryl-reactive iodoacetyl group, an MS-neutral spacer arm, and a first MS/MS reporter having a unique reporter ion mass. Excess label can be removed and the sample is denatured and reduced. The sample is then labeled with a second label having a sulfhydryl-reactive iodoacetyl group, an MS-neutral spacer arm, and a second MS/MS reporter having a unique reporter ion mass. The method includes enzymatically digesting the sample and analyzing the sample using an ultra-performance liquid chromatography tandem mass spectrometry system (UPLC-MS$^2$ system) including a charged surface hybrid column and a formic acid buffer mobile phase. Next, the method includes quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product. If a free thiol is detected, the protein drug product has disulfide heterogeneity. The method includes selecting the protein drug product that does not display disulfide heterogeneity. In one embodiment the first MS/MS reporter has a mass of 128 and the second MS/MS reporter has a mass of 131. The protein drug product is typically an antibody, for example a monoclonal, chimeric antibody, or a bispecific antibody, or antigen binding fragments thereof. Another embodiment provides a pharmaceutical composition containing the protein drug product selected using the method described above. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

BRIEF DESCRIPTION OF THE DRAWINGS

FIGS. 4A-4B are chromatogram results for MS$^2$ analysis of iodoTMT labeled peptides, specifically looking at TMT-tags 128/131. FIG. 4A is the complete chromatogram and FIG. 4B is a zoomed in on the TMT-tags 128/131. The X-axis represents time and the Y-axis represents relative abundance.

DETAILED DESCRIPTION OF THE INVENTION

I. Definitions

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx.+/−10%; in other embodiments the values may range in value either above or below the stated value in a range of approx.+/−5%; in other embodiments the values may range in value either above or below the stated value in a range of approx.+/−2%; in other embodiments the values may range in value either above or below the stated value in a range of approx.+/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by genetic engineering techniques (e.g., such as a sequence encoding a chimeric protein, or a codon-optimized sequence, an intronless sequence, etc.) where it may reside as an episome or be integrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713, which is incorporated by reference into this application.

"Hinge region" refers to the flexible amino acid stretch in the central part of the heavy chains of the IgG and IgA immunoglobulin classes, which links these 2 chains by disulfide bonds. In IgG immunoglobulins the hinge region is located between the CH1 and CH3 constant domains. The hinge region affords flexibility to the antibody, and allows easier binding to the antigen.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Rath, T., et al., *Crit Rev Biotech*, 35(2): 235-254 (2015), Levin, D., et al., *Trends Biotechnol*, 33(1): 27-34 (2015)) "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein comprises two or more distinct receptor chains that bind to a one or more ligand(s). For example, an Fc-fusion protein is a trap, such as for example an IL-1 trap or VEGF trap.

The term "disulfide bond" refers to the linkage formed by the oxidation of two SH groups, each attached to a cysteine. Disulfide bonds play an important role in the folding and stability of many proteins. IgGs include two heavy chains (HC) and two light chains (LC) covalently linked by a total of 16 inter- or intra-molecular disulfide bonds. IgG mAbs contain 32 cysteine residues, 5 cysteine residues on each LC and 11 cysteine residues on each HC. Each LC contains one variable domain and one constant domain with a disulfide bond connection. The $5^{th}$ cysteine on the LC is linked to either the $3^{rd}$ or $5^{th}$ cysteine of the HC to form an interchain disulfide bond. The heavy chains include an N-terminal variable domain (VH) and three constant domains (CH1, CH2, and CH3) with a hinge region between CH1 and CH2 (Vidarsson, G., et al., *Front Immunol*, 5:520 (2014)). The $6^{th}$ and $7^{th}$ cysteine on each HC are bonded forming the hinge region. The hinge region of an immunoglobulin helps form the Y-shaped structure of the immunoglobulin molecule. The Y shape makes possible the flexibility of the immunoglobulin molecules required in antigen binding.

The term "LC-MS" refers to liquid chromatography-mass spectrometry which is an analytical chemistry technique that combines the physical separation capabilities of liquid chromatography (or HPLC) with the mass analysis capabilities of mass spectrometry (MS). The term MS/MS or $MS^2$ refers to tandem mass spectrometry.

The term "free thiols" and "free sulfhydryls" are used interchangeably.

II. Methods of Identifying Free Thiols

Methods for identifying free thiols in proteins, including but not limited to antibodies are provided. A thiol or sulfhydryl generally refers to an organic compound containing the group SH. In proteins any two cysteines in close proximity will form a covalent bond, even cysteines that do not naturally pair together. This covalent bond between two cysteines is referred to as a disulfide bond. Disulfide bonds are critical for IgG tertiary structure, stability, and biological function. A free thiol or free sulfhydryl refers to a cysteine in a protein that is not part of a disulfide bond and can be indicative of improper structure formation in the protein which could result is adverse effects on protein drug potency, half-life, stability, or render the protein drug ineffective. Free sulfhydryls (also referred to as free thiols) can also occur as a result of incomplete disulfide bond formation or disulfide bond degradation. Increased free sulfhydryls can result in lower thermal stability and can affect binding affinity of antibodies to antigens by up to 50%. Disclosed herein are methods for identifying free sulfhydryls or free thiols.

A. Methods for Identifying Site Specific Free Thiols

Free thiols can exist in mAbs as a result of incomplete disulfide bond formation or disulfide bond breakage. The presence of free thiols can lower the thermal stability of mAb products and affect their structural integrity, stability, and biological functions. It is therefore important to characterize free thiols in mAb production. Methods for identifying site specific free thiols in protein drug products are disclosed herein. An exemplary method includes labeling peptides with a tag to identify free thiols and a tag to identify native disulfide bonds and analyzing the tags using targeted MS². In one embodiment, the method provides complete coverage of all 32 cysteine residues in an IgG molecule. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

One embodiment provides a method for identifying the presence of free thiols in a protein, for example an antibody or fragment thereof. An exemplary method for identifying free thiols in a protein drug product includes the steps of labeling a sample containing the protein drug product with a first label containing a sulfhydryl-reactive iodoacetyl group, an MS-neutral spacer arm, and a first MS/MS reporter having a unique reporter ion mass. Excess label can be removed and the sample is denatured and reduced. The sample is then labeled with a second label having a sulfhydryl-reactive iodoacetyl group, an MS-neutral spacer arm, and a second MS/MS reporter having a unique reporter ion mass. The method includes enzymatically digesting the sample and analyzing the sample using mass spectrometry, for example ultra-performance liquid chromatography tandem mass spectrometry system (UPLC-MS² system) including a charged surface hybrid column and a formic acid buffer mobile phase. Next, the method includes quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product. In one embodiment the first MS/MS reporter has a mass of 128 and the second MS/MS reporter has a mass of 131. The protein drug product is typically an antibody, for example a monoclonal or chimeric antibody. The presence of free thiols is likely a result of incomplete disulfide bond formation or disulfide bond degradation. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

Another embodiment provides a method of identifying disulfide heterogeneity in a protein drug product including the steps of labeling a sample containing the protein drug product with a first label containing a sulfhydryl-reactive iodoacetyl group, an MS-neutral spacer arm, and a first MS/MS reporter having a unique reporter ion mass. Excess label can be removed and the sample is denatured and reduced. The sample is then labeled with a second label having a sulfhydryl-reactive iodoacetyl group, an MS-neutral spacer arm, and a second MS/MS reporter having a unique reporter ion mass. The method includes enzymatically digesting the sample and analyzing the sample using mass spectrometry, for example an ultra-performance liquid chromatography tandem mass spectrometry system (UPLC-MS² system) including a charged surface hybrid column and a formic acid buffer mobile phase. Next, the method includes quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product. If the assay detects free thiols in the protein drug product, the protein drug product contains disulfide heterogeneity. The presence of these free thiols is likely a result of incomplete disulfide bond formation or disulfide bond degradation. In one embodiment the first MS/MS reporter has a mass of 128 and the second MS/MS reporter has a mass of 131. The protein drug product is typically an antibody, for example a monoclonal, chimeric antibody, bispecific antibody, or antigen binding fragments thereof. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

A method for selecting a protein drug product including the steps of labeling a sample containing the protein drug product with a first label containing a sulfhydryl-reactive iodoacetyl group, an MS-neutral spacer arm, and a first MS/MS reporter having a unique reporter ion mass. Excess label can be removed and the sample is denatured and reduced. The sample is then labeled with a second label having a sulfhydryl-reactive iodoacetyl group, an MS-neutral spacer arm, and a second MS/MS reporter having a unique reporter ion mass. The method includes enzymatically digesting the sample and analyzing the sample using an ultra-performance liquid chromatography tandem mass spectrometry system (UPLC-MS² system) including a charged surface hybrid column and a formic acid buffer mobile phase. Next, the method includes quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product. If a free thiol is detected, the protein drug products has disulfide heterogeneity. The method includes selecting the protein drug product that does not display disulfide heterogeneity. In another embodiment the selected protein drug product is an IgG that contains less than 5 free thiols, less than 4 free thiols, less than 3 free thiols, less than 2 free thiols. In some embodiments the free thiol is in a light chain of the IgG molecule. In some embodiments, the free thiol is in a heavy chain of the IgG molecule. In some embodiments, there is at least one free thiol in a light chain and at least one free thiol in a heavy chain of the IgG molecule. In one embodiment the first MS/MS reporter has a mass of 128 and the second MS/MS reporter has a mass of 131. The protein drug product is typically an antibody, for example a monoclonal, chimeric antibody, or a bispecific antibody, or antigen binding fragments thereof. Another embodiment provides a pharmaceutical composition containing the protein drug product selected using the method described above. In one embodiment, the method provides complete coverage of all 32 cysteine residues in an IgG molecule. In other embodiments the method covers the 16 cysteine residues on the heavy and light chains in an IgG molecule. In another embodiment, the method covers the 5 cysteine residues on each light chain of an IgG molecule. In another embodiment, the method covers the 11 cysteine residues on each heavy chain of an IgG molecule.

1. Iodoacetyl Tags

In one embodiment, peptides can be labeled with tags to identify native disulfide bonds and free thiol residues. The tag can be an iodoacetyl tag that labels cysteine-containing peptides. Exemplary tags include but are not limited to Thermo Scientific™ Iodoacetyl Tandem Mass Tag™ (iodoTMT™). Iodoacetyl tags irreversibly label free sulfhydryl groups on cysteine residues. The tags include a sulfhydryl-reactive iodoacetyl group, a mass normalizer arm, and a MS/MS reporter. A total of five isotope atoms made of a combination of 13C and 15N are incorporated into the mass normalizer arm and the MS/MS reporter region in each reagent but distributed at different locations as labeled by asterisks in FIG. 1A. As a result, each reagent has the same nominal parent mass but a unique mass for MS/MS reporter region that could be differentiated on MS/MS spectra: 127 Da, 128 Da, 130 Da and 131 Da. In one embodiment, free thiol is tagged with a label having a mass of 126, 127, 128, 129, 130, or 131 Da. In another embodiment, native disulfide bonds are tagged with a label having a mass that is different from the mass label used to detect the free thiol. A non-limiting example includes a free thiol tagged with a label having a mass of 127 Da, and a native disulfide bond tagged with a label having a mass of 130 Da.

Figure 1A:
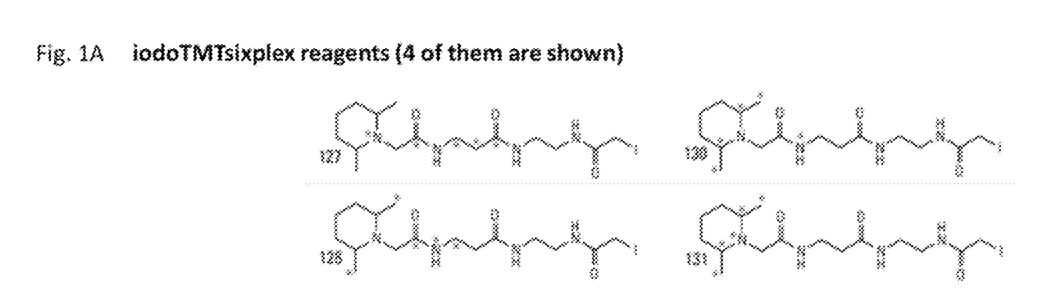
FIG. 1A is a schematic illustration of four IodoTMTsixplex reagents.
Figures 1A, 1B:
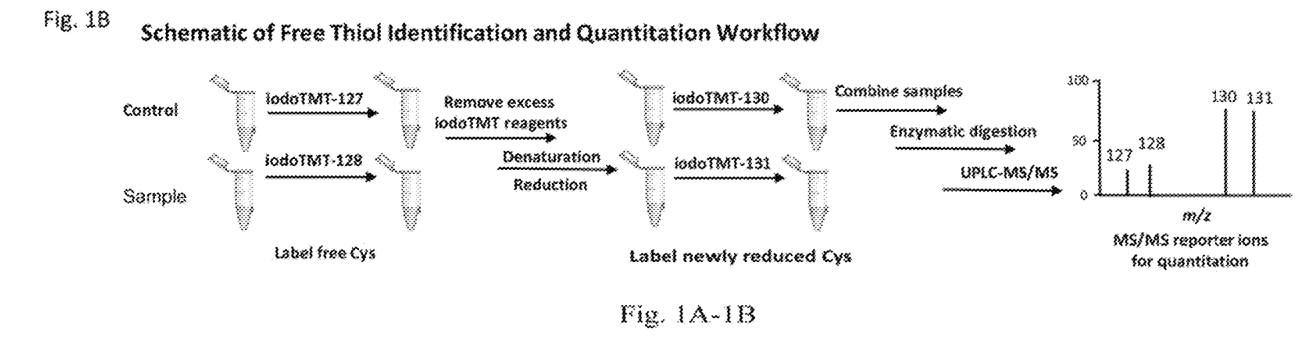
FIG. 1B is a schematic illustration of an exemplary workflow for labeling peptides with iodoTMT labels.

An exemplary workflow is provided in FIG. 1B. In one embodiment, an aliquot of the peptide sample is mixed with the first tag and incubated. Excess reagent can be removed from the sample and the sample can be denatured and reduced. In one embodiment, the second mass tag is added to the sample after denaturing the sample. The sample can be enzymatically digested after addition of the second tag. Exemplary methods for enzymatic digestion were discussed above. In another embodiment, the two samples can be added together before further analysis. In some embodiments, up to three pairs of tags can be analyzed in a single run.

2. MS/MS

In one embodiment, the iodoacetyl tag labeled peptides are analyzed using mass spectrometry, for example ultra performance liquid chromatography (UPLC)-MS/MS. In one embodiment, the UPLC is performed on an ethylene bridged hybrid (BEH) column or a charged surface hybrid (CSH) column. The buffers can be trifluoroacetic acid (TFA) buffers or formic acid (FA) buffers. The liquid chromatography can be run for about 90 minutes to about 150 minutes. It will be appreciated that buffers and run times can be optimize of the particular sample being analyzed. In some embodiments, the run includes a re-equilibration step of about 40 minutes. In a preferred embodiment, the UPLC is run on a 150 mm CSH column using FA buffers for 150 minutes with a 40 minute re-equilibration step.

Figure 2:
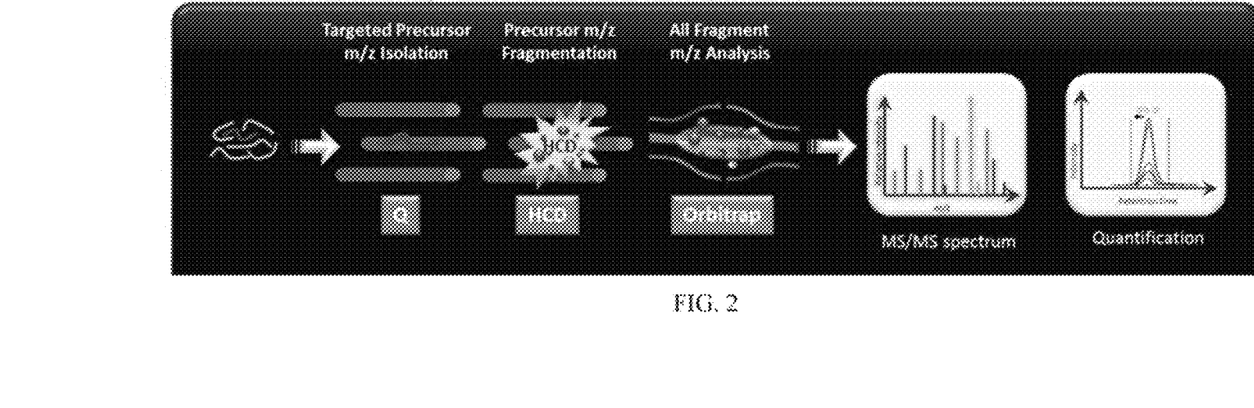
FIG. 2 is a schematic illustration of an exemplary workflow for analyzing iodoTMT labeled peptides using targeted MS$^2$.

After the peptides are separated using UPLC, they can be analyzed using mass spectroscopy. In a preferred embodiment, targeted $MS^2$ spectrometry is used. The mass spectrometer can be, for example, a Thermo Scientific Q Exactive hybrid quadrupole Orbitrap® mass spectrometer. An exemplary workflow for targeted $MS^2$ is shown in FIG. 10. The peptides can be introduced into the mass spectrometer and analyzed using parallel reaction monitoring. In one embodiment, precursor mass filtering is performed in Q1 followed by fragmentation in the HCD cell and high resolution/high mass accuracy (HR/HA) fragment ion detection in the Orbitrap® mass analyzer. In some embodiments, the peptides are captured in $MS^1$ to verify the correct peptide at the correct mass. The reporter label is broken off of the peptide in the Orbitrap® of $MS^2$ and is then quantified in the Orbitrap. The relative abundance of each cysteine corresponding to the detected mass tag can be calculated.

In one embodiment, inclusion masses are included in the $MS^2$ scan. For example, the masses of specific cysteines of interest or concern can be programmed into an inclusion list. In one embodiment, the use of an inclusion list can more intensely quantify the residues of interest. In another embodiment, exclusion masses are excluded from the $MS^2$ scan. For example, the masses of specific cysteines that are known to be stable or rarely form scrambled bonds can be excluded from the scan.

C. Proteins of Interest

In one embodiment the protein of interest is a protein drug product or is a protein of interest suitable for expression in prokaryotic or eukaryotic cells. For example, the protein can be an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins in the complexes may be simple polypeptides consisting of a single subunit, or complex multi subunit proteins comprising two or more subunits. The protein of interest may be a biopharmaceutical product, food additive or preservative, or any protein product subject to purification and quality standards In some embodiments, the protein of interest is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a dual-specific, tetravalent immunoglobulin G-like molecule, termed dual variable domain immunoglobulin (DVD-IG), an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In another embodiment, the antibody comprises a chimeric hinge. In still other embodiments, the antibody comprises a chimeric Fc. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g., an anti-PD-L1 antibody as described in in U.S. Pat. Appln. Pub. No. US2015/0203580A1), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-C5 antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g., an anti-PCSK9 antibody as described in U.S. Pat. No. 8,062,640 or 9,540,449), an Anti-Growth and Differentiation Factor-8 antibody (e.g. an anti-GDF8 antibody, also known as anti-myostatin antibody, as described in U.S. Pat. No. 8,871,209 or 9,260,515), an anti-Glucagon Receptor (e.g. anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. No. 8,735,095 or 8,945,559), an anti-interleukin 6 receptor antibody (e.g., an anti-IL6R antibody as described in U.S. Pat. No. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. No. 9,453,072 or 9,637,535), an anti-Respiratory syncytial virus antibody (e.g., anti-RSV antibody as described in U.S. Pat. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel dl antibody (e.g. as described in U.S. Pat. No. 9,079,948), an anti-Middle East Respiratory Syndrome virus (e.g. an anti-MERS antibody as described in U.S. Pat. Appln. Pub. No. US2015/0337029A1), an anti-Ebola virus antibody (e.g. as described in U.S. Pat. Appln. Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. Appln. Pub. No. US2016/0017029 and U.S. Pat. Nos. 8,309,088 and 9,353,176) and an anti-Protein Y antibody. In some embodiments, the bispecific antibody is selected from the group consisting of an anti-CD3×anti-CD20 bispecific antibody (as described in U.S. Pat. Appln. Pub. Nos. US2014/0088295A1 and US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is herein incorporated by reference in its entirety), or a VEGF trap (e.g., aflibercept or ziv-aflibercept, which comprises the Ig domain 2 of the VEGF receptor Flt1 fused to the Ig domain 3 of the VEGF receptor Flk1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

D. Producing mAb with Little or No Disulfide Heterogeneity

One embodiment provides methods of producing a protein drug product containing little or no free thiols. An exemplary method includes culturing cells producing the antibody in a cell culture under suitable conditions to produce the antibody, purifying the antibody under suitable conditions to extract the antibody, admixing the antibody with excipients under suitable conditions to stabilize the antibody, obtaining a sample of the antibody from the cell culture, following purification of the antibody from the cell culture, or following the addition of excipients to the purified antibody, characterizing disulfide bonds of the antibody according to the disclosed methods, and modifying one or more cell culture, purification or excipient conditions to reduce the amount of crossed hinge disulfide bonds of the antibody.

The one or more cell culture, purification, or excipient conditions that are changed to reduce the amount of free thiols in the antibody include but are not limited to temperature, pH, oxygen levels, reactive oxygen species, surfactants, or combinations thereof. In one embodiment, an amino acid free strategy of cell culture could affect disulfide bond formation.

In one embodiment, the cells producing the antibody are Chinese hamster ovary cells. In another embodiment, the cells are hybridoma cells. In embodiment, the protein drug product is an IgG monoclonal antibody are a fragment thereof.

In one embodiment, the protein drug product contains no free thiols. In another embodiment the protein drug product contains less than 5 free thiols, less than 4 free thiols, less than 3 free thiols, less than 2 free thiols in an IgG molecule. In some embodiments the free thiol is in a light chain of an IgG molecule. In some embodiments, the free thiol is in a heavy chain of an IgG molecule. In some embodiments, there is at least one free thiol in a light chain and at least one free thiol in a heavy chain of an IgG molecule.

EXAMPLES

Example 1: Analysis of Site-Specific Free Thiols

Methods

Cysteine Labeling

The workflow from FIG. 1B was followed. In brief, a control sample and an antibody sample were labeled with iodo-TMT reagents (FIG. 1A). The excess reagents were removed and the samples were denatured and reduced using 0.5M TCEP and incubated for 1 hour. After denaturation and reduction, a second label was added to the samples. The samples were then combined, enzymatically digested, and analyzed using UPLC-MS/MS. UPLC conditions were as follows: Samples were run on a 150 mm CSH column for a 150 minutes run, including a 40 minute re-equilibration step. FA buffers were used.

Spike-in Study

For the spike-in study, aliquots of two different samples of the same protein were prepared. The proteins were denatured using GuanHCl and reduced. The samples were labeled with two different IodoTMT tags. A spike-in concentration gradient was then prepared. 10%, 5%, 1%, 0.5%, or 0.1% of protein sample 1 was added to aliquots of protein sample 2. The samples were then enzymatically digested and analyzed using UPLC/MS-MS (FIG. 2).

Results:

Table 1 shows the results from targeted $MS^2$ analysis of a Regeneron antibody labeled with iodo-TMT tags to identify site-specific free thiols. As can be seen in the table, all sixteen cysteine residues were identified.

Figure 3A:
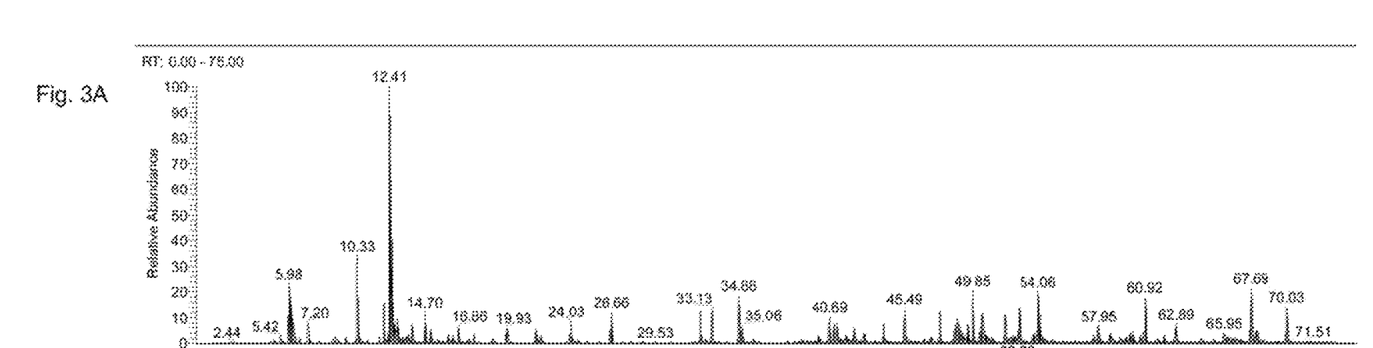
FIGS. 3A-3B are chromatogram results from MS$^2$ analysis of iodoTMT labeled peptides run with data dependent run (FIG. 3A) or a targeted MS$^2$ with inclusion list (FIG. 3B). The X-axis represents time and the Y-axis represents relative abundance.
Figure 3B:
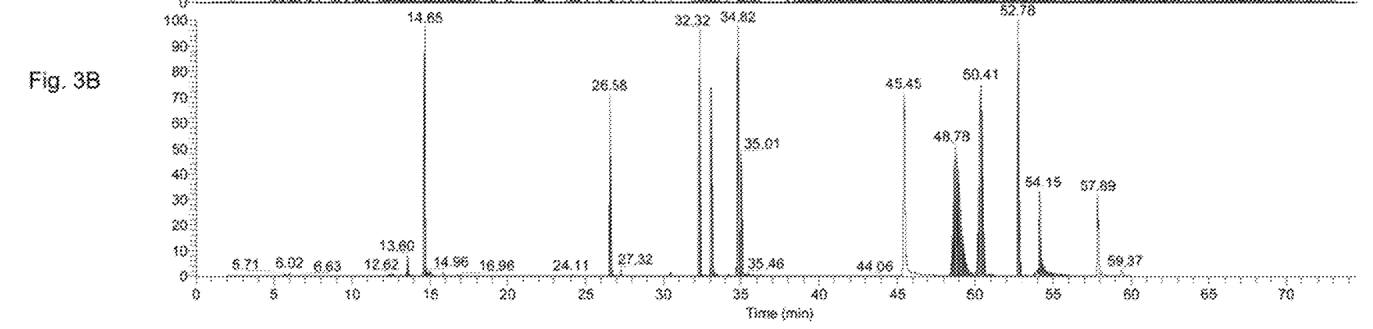
Figure 4A:
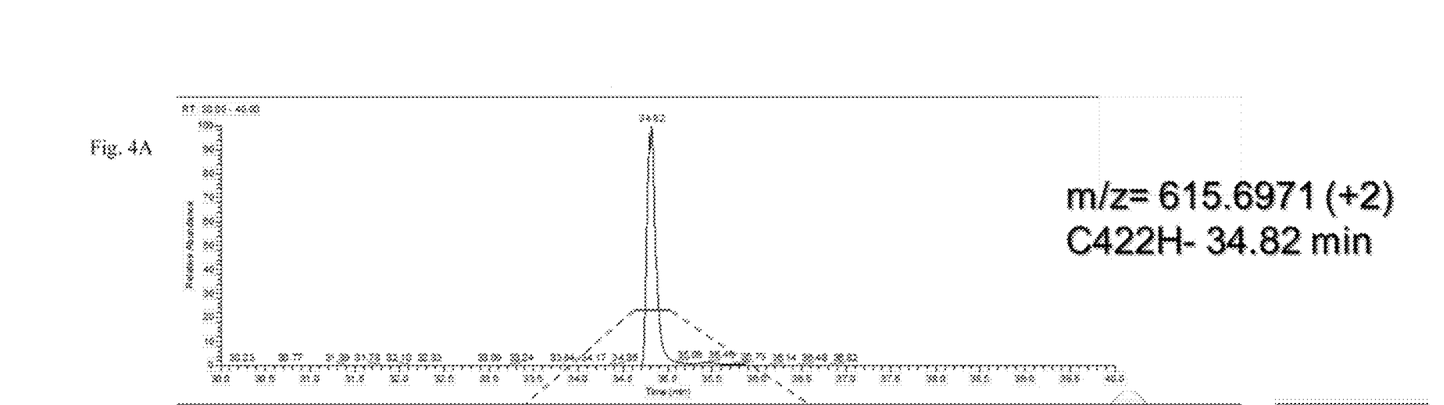
Figure 4B:
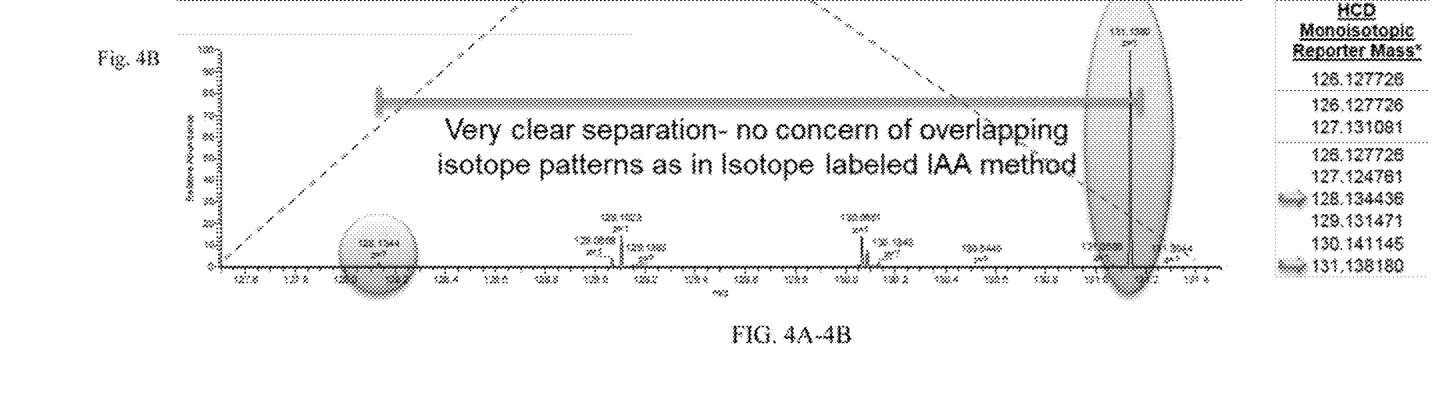
Figure 5A:
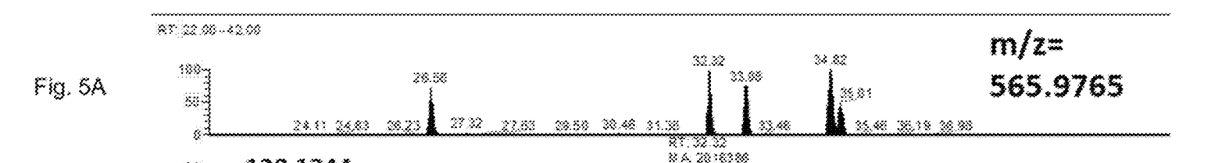
FIGS. 5A-5G are chromatogram results from MS$^2$ analysis of iodoTMT labeled peptides from different lots of an antibody. The X-axis represents time and the Y-axis represents relative abundance.
Figure 5B:
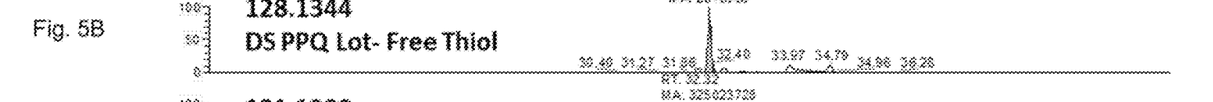
Figure 5C:
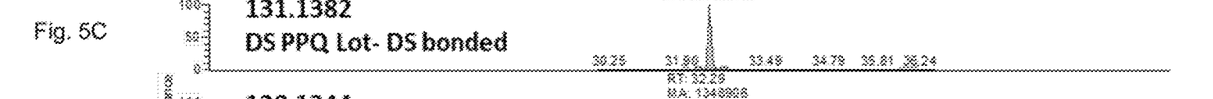
Figure 5D:
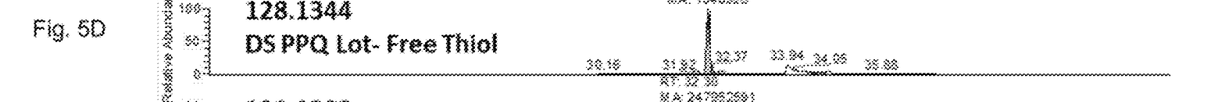
Figure 5E:
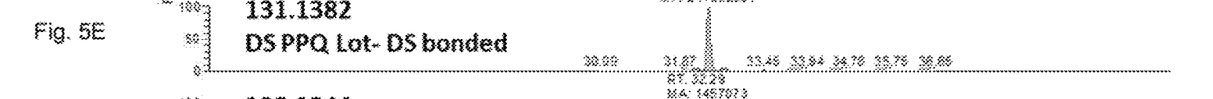
Figure 5F:
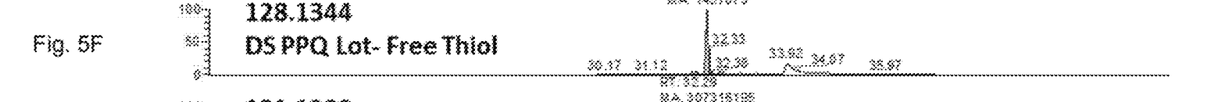
Figure 5G:
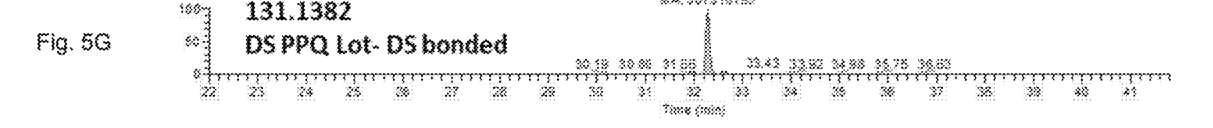

FIGS. 3A-3B show a comparison of data dependent $MS^2$ run and a targeted $MS^2$ run (with an inclusion list) for the same sample. As shown in the figures, targeted $MS^2$ run with an inclusion list of specific cysteines can help to more intensely quantify specific cysteine residues. In addition, the use of the iodo-TMT tags coupled with targeted $MS^2$ allows for better separation of labeled cysteines. FIG. 4A-4B shows clear separation of 128 Da labeled cysteine and a 131 Da labeled cysteine. The disclosed method has very clear separation with no concern of overlapping isotope patterns as is seen in current methods such as labeled IAA methods.

To further show the utility of the disclosed method, different lots of the same antibody product were compared. FIGS. 5A-5G show the relative abundance of free thiols and disulfide bonded cysteines in different lots of the same antibody.

Figure 6:
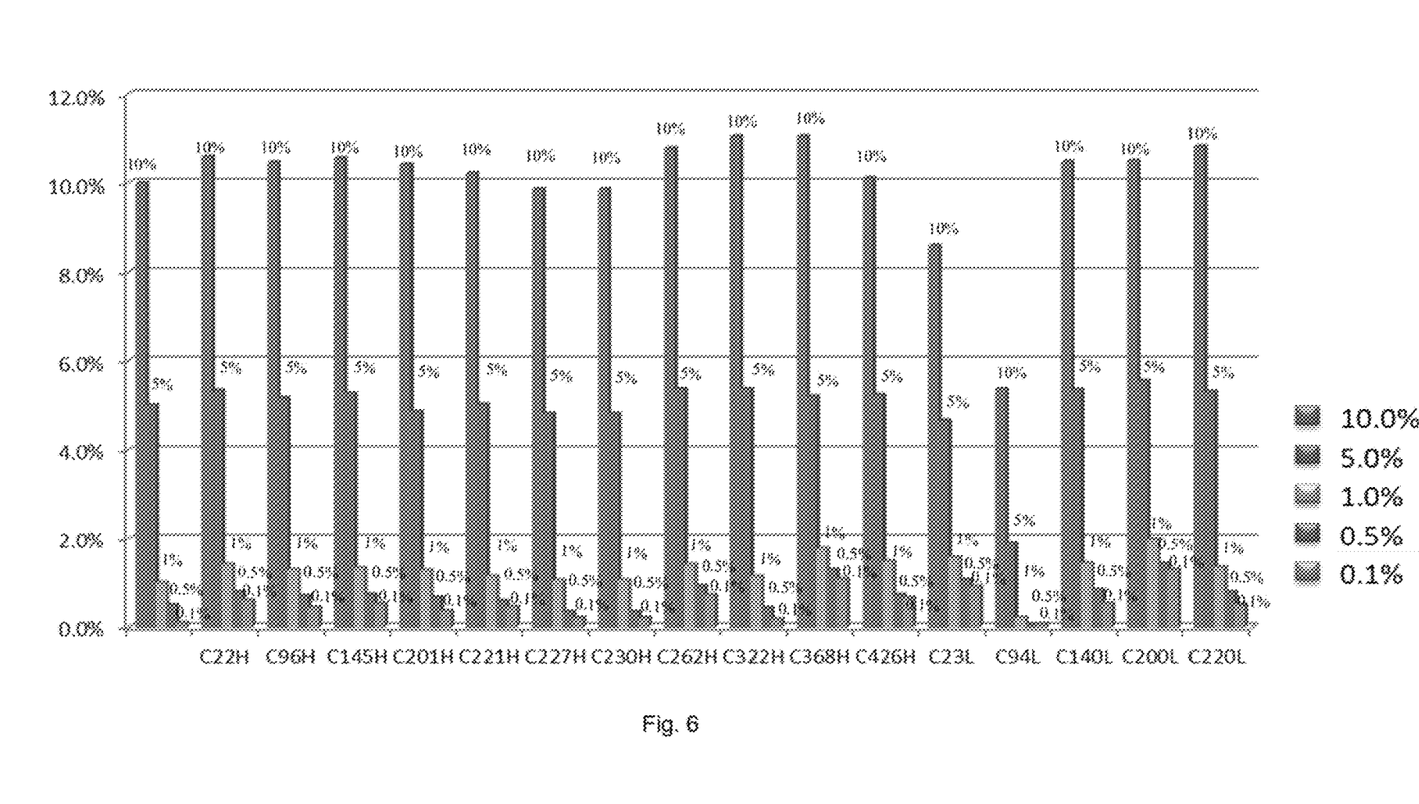
FIG. 6 is a bar graph showing relative abundance of various cysteine residues from a spike-in study in which 10%, 5%, 1%, 0.5%, or 0.1% of protein sample 1 was spiked into protein sample 2.

Additional validation of the method was performed using a spike-in study. Various percentages of labeled protein sample 1 were added into labeled protein sample 2. FIG. 6 shows the results of the spike-in study. The majority of the cysteines showed the expected amount of free thiols that would be predicted by the amount of protein sample 1 spiked into protein sample 2, indicating that the method is effective at predicting relative abundance of free thiols.

TABLE 1

Targeted $MS^2$ Results

| Mass [m/z] | Polarity | Start [min] | End [min] | NCE | CS [z] | Comment | Retention Time |
|---|---|---|---|---|---|---|---|
| 827.7385 | Positive | 57 | 63 | 30 | 3 | C22H- 2481.2010 | 60.57 |
| 781.8890 | Positive | 30 | 36 | 30 | 2 | C96H- 1562.7694 | 33.72 |
| 797.4441 | Positive | 40 | 46 | 30 | 2 | C145H- 1593.8809 | 43.90 |
| 1748.1358 | Positive | 72 | 78 | 30 | 4 | C201H- 6985.5196 | 75.62 |
| 391.2077 | Positive | 10 | 16 | 30 | 2 | C221H- 781.4062 | 14.70 |
| 1130.2953 | Positive | 58 | 64 | 30 | 3 | C227H/C230H- 3388.8659 | 62.23 |
| 804.4156 | Positive | 45 | 51 | 30 | 3 | C262H- 2411.2322 | 48.67 |
| 500.2775 | Positive | 16 | 22 | 30 | 2 | C322H- 999.5477 | 19.64 |
| 717.4208 | Positive | 42 | 48 | 30 | 2 | C368H-1433.8334 | 46.23 |
| 1025.4963 | Positive | 46 | 52 | 30 | 3 | C426H- 3073.4685 | 50.15 |
| 489.7835 | Positive | 20 | 26 | 30 | 2 | C23L- 978.5581 | 23.53 |
| 1637.7747 | Positive | 64 | 70 | 30 | 3 | C94L- 4911.3185 | 67.71 |
| 690.7049 | Positive | 60 | 66 | 30 | 3 | C140L- 2070.1001 | 63.31 |
| 716.7147 | Positive | 35 | 41 | 30 | 3 | C200L- 2148.1294 | 38.98 |
| 571.2846 | Positive | 22 | 28 | 30 | 2 | C220L- 1141.5597 | 25.24 |

Figure 7:
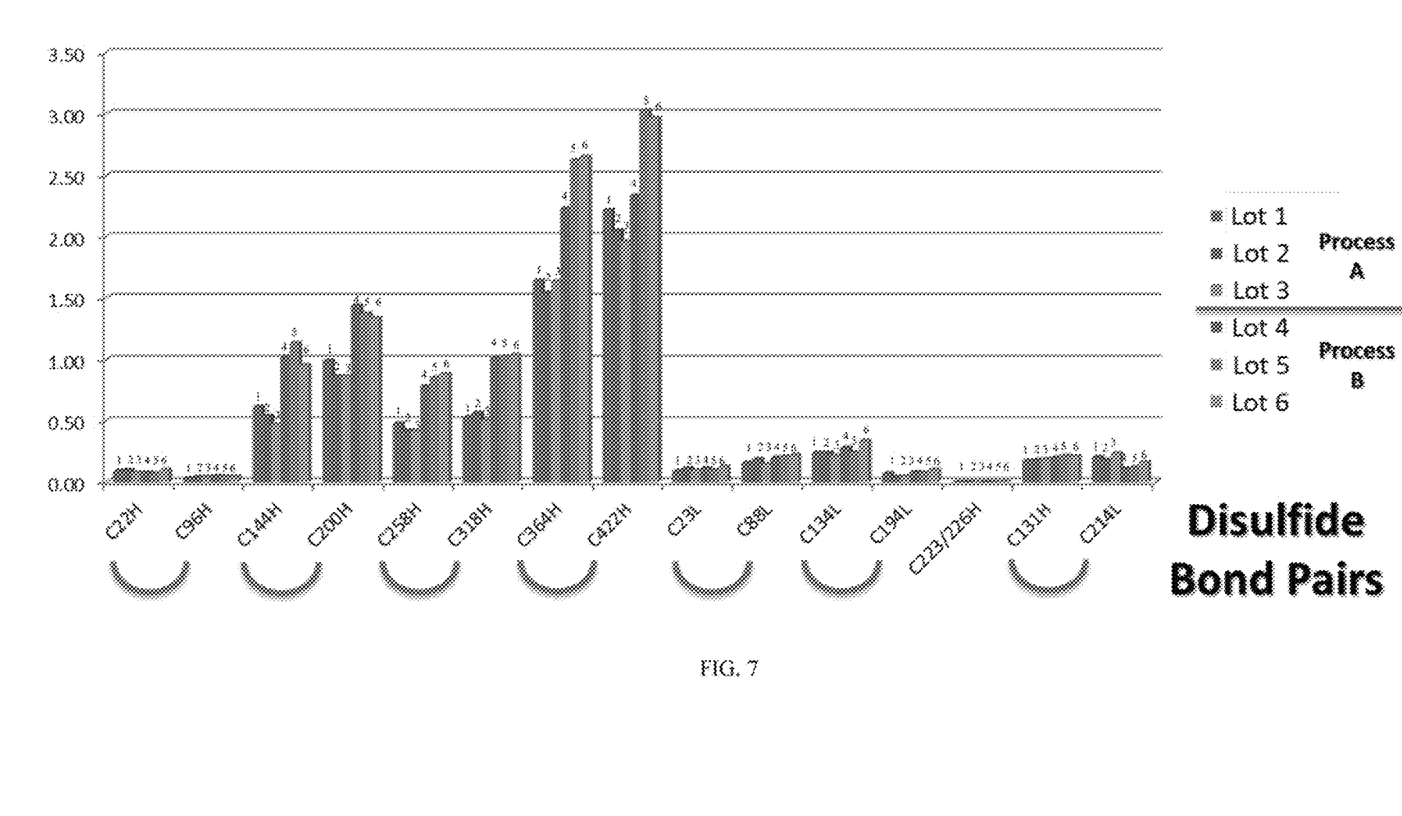
FIG. 7 is a bar graph showing relative abundance of various cysteine disulfide bond pairs in antibody Lots 1-3 of production process A and antibody Lots 4-6 of production process B. Disulfide bond pairs are indicated by curved lines connecting the two cysteines.

Table 2 summarizes the results of free thiol and disulfide bond abundance for a Regeneron antibody product. Site specific free thiol percentages were calculated for each cysteine site. All sixteen cysteines were identified and quantified. A threshold of 5-6% free thiols was set, anything below the threshold does not show a potential for disulfide bond breakage. FIG. 7 presents the relative abundance of disulfide bond pairs in different lots of a Regeneron antibody product.

The disclosed methods and results can be used for site-specific total free thiol quantitation and as a potential indicator of disulfide scrambling locations. In addition it can be used to identify intrachain disulfides leading to half molecule or aggregation.

TABLE 2

Process comparability.

| Disulfide Bond | | Site Specific Free Thiol Content (%) | | | | | | | |
|---|---|---|---|---|---|---|---|---|---|
| | | Process A | | | Process B | | | | STD |
| Disulfide Bond | Cys Site | Lot 1 | Lot 2 | Lot 3 | Lot 4 | Lot 5 | Lot 6 | Avg | Dev |
| C22H-C96H | C22H | 0.09 | 0.10 | 0.08 | 0.08 | 0.07 | 0.10 | 0.09 | 0.01 |
| | C96H | 0.03 | 0.04 | 0.04 | 0.05 | 0.05 | 0.05 | 0.04 | 0.01 |

TABLE 2-continued

Process comparability.

| Disulfide Bond | | Site Specific Free Thiol Content (%) | | | | | | | |
|---|---|---|---|---|---|---|---|---|---|
| | | Process A | | | Process B | | | | STD |
| Disulfide Bond | Cys Site | Lot 1 | Lot 2 | Lot 3 | Lot 4 | Lot 5 | Lot 6 | Avg | Dev |
| C144H-C200H | C144H | 0.62 | 0.54 | 0.47 | 1.02 | 1.13 | 0.96 | 0.79 | 0.21 |
| | C200H | 0.99 | 0.87 | 0.87 | 1.44 | 1.37 | 1.34 | 1.15 | 0.24 |
| C258H-C318H | C258H | 0.48 | 0.42 | 0.42 | 0.78 | 0.86 | 0.88 | 0.64 | 0.15 |
| | C318H | 0.53 | 0.57 | 0.50 | 1.02 | 1.03 | 1.04 | 0.78 | 0.21 |
| C364H-C422H | C364H | 1.64 | 1.54 | 1.64 | 2.23 | 2.63 | 2.65 | 2.05 | 0.27 |
| | C422H | 2.22 | 2.05 | 1.96 | 2.34 | 3.03 | 2.97 | 2.43 | 0.14 |
| C23L-C88L | C23L | 0.09 | 0.11 | 0.10 | 0.11 | 0.10 | 0.13 | 0.11 | 0.01 |
| | C88L | 0.16 | 0.19 | 0.15 | 0.20 | 0.21 | 0.22 | 0.19 | 0.02 |
| C134L-C194L | C134L | 0.24 | 0.24 | 0.22 | 0.28 | 0.24 | 0.34 | 0.26 | 0.02 |
| | C194L | 0.07 | 0.04 | 0.05 | 0.08 | 0.08 | 0.10 | 0.07 | 0.02 |
| Hinge | C223H/226H | 0.00 | 0.00 | 0.00 | 0.00 | 0.00 | 0.00 | 0.00 | 0.00 |
| C131H-C214L | C131H | 0.18 | 0.18 | 0.19 | 0.20 | 0.22 | 0.21 | 0.20 | 0.01 |
| | C214L | 0.20 | 0.18 | 0.24 | 0.11 | 0.12 | 0.17 | 0.17 | 0.05 |

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for identifying free thiols in a protein drug product, comprising:
    labeling a sample comprising a protein drug product with a first label comprising a sulfhydryl-reactive iodoacetyl group, an MS-neutral spacer arm, and a first MS/MS reporter having a unique reporter ion mass;
    removing excess first label;
    denaturing and reducing the sample;
    labeling the sample with a second label comprising a sulfhydryl-reactive iodoacetyl group, an MS-neutral spacer arm, and a second MS/MS reporter having a unique reporter ion mass;
    enzymatically digesting the sample;
    analyzing the sample using an UPLC-MS$^2$ system comprising a charged surface hybrid column and a formic acid buffer mobile phase; and
    quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product, wherein a threshold of 5-6% free thiols was set, and wherein a result below the threshold does not show a potential for disulfide bond breakage.

2. The method of claim 1, wherein the first MS/MS reporter has a mass of 128 and the second MS/MS reporter has a mass of 131.

3. The method of claim 1, wherein the first and second labels are selected from the group consisting of 4. The method of claim 1, wherein the method provides complete coverage of all 32 cysteine residues in an IgG molecule.

5. The method of claim 1, wherein the method covers the 16 cysteine residues on the heavy and light chains in an IgG molecule.

6. The method of claim 1, wherein the method covers the 5 cysteine residues on each light chain of an IgG molecule.

7. The method of claim 1, wherein the method covers the 11 cysteine residues on each heavy chain of an IgG molecule.

8. A method of identifying disulfide heterogeneity in a protein drug product comprising the steps of:
labeling a sample comprising a protein drug product with a first label comprising a sulfhydryl-reactive iodoacetyl group, an MS-neutral spacer arm, and a first MS/MS reporter having a unique reporter ion mass;
removing excess first label;
denaturing and reducing the sample;
labeling the sample with a second label comprising a sulfhydryl-reactive iodoacetyl group, an MS-neutral spacer arm, and a second MS/MS reporter having a unique reporter ion mass;
enzymatically digesting the sample;
analyzing the sample using an UPLC-MS$^2$ system comprising a charged surface hybrid column and a formic acid buffer mobile phase; and
quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product, wherein the detection of a free thiol indicates the protein drug product has disulfide heterogeneity, wherein a threshold of 5-6% free thiols was set, and wherein a result below the threshold does not show a potential for disulfide bond breakage.

9. The method of claim 8, wherein the first and second labels are selected from the group consisting of 10. The method of claim 8, wherein the method provides complete coverage of all 32 cysteine residues in an IgG molecule.

11. The method of claim 8, wherein the method covers the 16 cysteine residues on the heavy and light chains in an IgG molecule.

12. The method of claim 8, wherein the method covers the 5 cysteine residues on each light chain of an IgG molecule.

13. The method of claim 8, wherein the method covers the 11 cysteine residues on each heavy chain of an IgG molecule.

14. A method for selecting a protein drug product comprising the steps of:
labeling a sample comprising a protein drug product with a first label comprising a sulfhydryl-reactive iodoacetyl group, an MS-neutral spacer arm, and a first MS/MS reporter having a unique reporter ion mass;
removing excess first label;
denaturing and reducing the sample;
labeling the sample with a second label comprising a sulfhydryl-reactive iodoacetyl group, an MS-neutral spacer arm, and a second MS/MS reporter having a unique reporter ion mass;
enzymatically digesting the sample;
analyzing the sample using an UPLC-MS$^2$ system comprising a charged surface hybrid column and a formic acid buffer mobile phase;
quantifying the first MS/MS reporter and the second MS/MS reporter, wherein the amount of the first MS/MS reporter correlates to the amount of free thiols in the protein drug product and the amount of the second MS/MS reporter correlates to the amount of bound thiols in the protein drug product, wherein a threshold of 5-6% free thiols was set, and wherein a result below the threshold does not show a potential for disulfide bond breakage; and
selecting the protein product if it has little or no free thiols.

15. The method of claim 14, wherein the selected protein drug product contains less than 5 free thiols, less than 4 free thiols, less than 3 free thiols, or less than 2 free thiols in an IgG molecule.

16. The method of claim 15, wherein the free thiol is in a light chain of an IgG molecule.

17. The method of claim 15, wherein the free thiol is in a heavy chain of an IgG molecule.

18. The method of claim 15, wherein at least one free thiol is in a light chain and at least one free thiol is in a heavy chain of an IgG molecule.

19. The method of claim 1, wherein the UPLC-MS$^2$ system comprises an ethylene bridged hybrid (BEH) column and a formic acid buffer mobile phase.

20. The method of claim 1, wherein the sample is analyzed for about 90 minutes to about 150 minutes.

21. The method of claim 1 further comprising equilibrating the sample.

22. The method of claim 21, wherein the sample is equilibrated for 40 minutes.

* * * * *

UNITED STATES PATENT AND TRADEMARK OFFICE
CERTIFICATE OF CORRECTION

| | |
|---|---|
| PATENT NO. | : 11,674,968 B2 |
| APPLICATION NO. | : 16/745020 |
| DATED | : June 13, 2023 |
| INVENTOR(S) | : Sook Yen E et al. |

It is certified that error appears in the above-identified patent and that said Letters Patent is hereby corrected as shown below:

On the Title Page

At Item (73), Assignee Name should be corrected to:
(73) Assignee: Regeneron Pharmaceuticals, Inc.,
Tarrytown, NY (US)

Signed and Sealed this
First Day of August, 2023

Katherine Kelly Vidal
*Director of the United States Patent and Trademark Office*